US008618176B2

(12) United States Patent
Podolski

(10) Patent No.: US 8,618,176 B2
(45) Date of Patent: *Dec. 31, 2013

(54) METHODS AND MATERIALS FOR THE TREATMENT OF TESTOSTERONE DEFICIENCY IN MEN

(75) Inventor: Joseph S. Podolski, The Woodlands, TX (US)

(73) Assignee: Repros Therapeutics Inc., The Woodlands, TX (US)

( * ) Notice: Subject to any disclaimer, the term of this patent is extended or adjusted under 35 U.S.C. 154(b) by 568 days.

This patent is subject to a terminal disclaimer.

(21) Appl. No.: 12/838,036

(22) Filed: Jul. 16, 2010

(65) Prior Publication Data

US 2010/0286281 A1 Nov. 11, 2010

Related U.S. Application Data

(62) Division of application No. 10/483,458, filed as application No. PCT/US02/21524 on Jul. 9, 2002, now Pat. No. 7,759,360.

(60) Provisional application No. 60/304,313, filed on Jul. 9, 2001.

(51) Int. Cl.
*A61K 31/13* (2006.01)
*A61K 9/20* (2006.01)

(52) U.S. Cl.
USPC ........................................... 514/651; 424/465

(58) Field of Classification Search
None
See application file for complete search history.

(56) References Cited

U.S. PATENT DOCUMENTS

| 2,914,563 A | 11/1959 | Allen et al. |
| 4,061,733 A | 12/1977 | Gunjikar |
| 4,729,999 A | 3/1988 | Young |
| 4,820,736 A | 4/1989 | Jensen et al. |
| 4,894,373 A | 1/1990 | Young |
| 5,728,688 A | 3/1998 | Labrie |
| 5,861,389 A | 1/1999 | Radlmaier |
| 6,017,964 A | 1/2000 | MacLean et al. |
| 6,096,338 A | 8/2000 | Lacy |
| 6,126,969 A | 10/2000 | Shah |
| 6,129,933 A | 10/2000 | Oshlack |
| 6,143,353 A | 11/2000 | Oshlack |
| 6,190,591 B1 | 2/2001 | Van Lengerich |
| 6,221,399 B1 | 4/2001 | Rolfes |
| 6,248,363 B1 | 6/2001 | Patel |
| 6,291,505 B1 | 9/2001 | Huebner et al. |
| 6,342,250 B1 | 1/2002 | Masters |
| 6,391,920 B1 | 5/2002 | Fisch |
| 6,511,986 B2 | 1/2003 | Zhang et al. |
| 6,583,129 B1 | 6/2003 | Mazer et al. |
| 6,600,010 B2 | 7/2003 | Mao et al. |
| 6,638,528 B1 | 10/2003 | Kanios |
| 6,645,974 B2 | 11/2003 | Hutchinson et al. |
| 6,653,297 B1 | 11/2003 | Hodgen |
| 6,685,957 B1 | 2/2004 | Bezemer et al. |
| 6,743,448 B2 | 6/2004 | Kryger |
| 7,105,679 B2 | 9/2006 | Kanojia et al. |
| 7,354,581 B2 | 4/2008 | Cedarbaum et al. |
| 2002/0120012 A1 | 8/2002 | Fisch |
| 2002/0183296 A1 | 12/2002 | Dudley et al. |
| 2004/0097597 A1 | 5/2004 | Podolski et al. |
| 2004/0171697 A1 | 9/2004 | Podolski et al. |
| 2004/0220154 A1 | 11/2004 | Kryger |
| 2004/0241224 A1 | 12/2004 | Podolski et al. |
| 2006/0269611 A1 | 11/2006 | Steiner et al. |
| 2009/0099265 A1 | 4/2009 | van As |
| 2009/0215906 A1 | 8/2009 | Podolski |
| 2010/0111901 A1 | 5/2010 | Gant et al. |
| 2010/0144687 A1 | 6/2010 | Glaser |

FOREIGN PATENT DOCUMENTS

| AU | 200261684 B2 | 12/2001 |
| EP | 0206021 B1 | 8/1988 |
| EP | 0430388 A2 | 6/1991 |
| EP | 0888775 A2 | 7/1999 |
| EP | 1090639 A2 | 4/2001 |
| EP | 1829534 A1 | 3/2006 |
| JP | 4-312522 | 11/1992 |
| JP | 2005-520779 | 7/2005 |
| WO | WO 95/35093 | 12/1995 |
| WO | WO 01/34117 A1 | 5/2001 |
| WO | WO 01/91744 A1 | 12/2001 |
| WO | 02/30355 | 4/2002 |
| WO | 03/005954 A3 | 1/2003 |
| WO | WO 03/005954 A2 | 1/2003 |
| WO | WO 03/005954 A3 | 1/2003 |
| WO | WO 03/026568 A2 | 4/2003 |
| WO | WO 03/072092 | 9/2003 |
| WO | 2006/019916 A1 | 2/2006 |
| WO | 2006/084153 A2 | 8/2006 |
| WO | 2006/102232 A2 | 9/2006 |
| WO | 2007/019165 A1 | 2/2007 |

(Continued)

OTHER PUBLICATIONS

Wang, C, et al., Fertil Steril. Sep. 1983; 40(3):358-65.*

(Continued)

*Primary Examiner* — Scott Long
*Assistant Examiner* — Lyndsey Beckhardt
(74) *Attorney, Agent, or Firm* — Morgan, Lewis & Bockius LLP

(57) ABSTRACT

The present invention relates to the use of compositions comprising trans-clomiphene for treating men with hypogonadism. The invention is also directed to methods for treating males with hypogonadism.

7 Claims, 3 Drawing Sheets

(56) References Cited

FOREIGN PATENT DOCUMENTS

| | | |
|---|---|---|
| WO | 2009/051908 A1 | 4/2009 |
| WO | 2010/054248 | 5/2010 |
| WO | 2013/020215 | 2/2013 |

OTHER PUBLICATIONS

Healthline, Hypogonadotropic hypogonadism, accessed Oct. 15, 2010, pp. 1-2.*
Ross, J. W. et al., "Effect of Clomiphene Citrate and Its Isomers on Sexual Behavior in Ovariectomized Rats", Endocrinology, vol. 92(4): 1079-1083, (abstract).*
Ben-Jonathan, N., et al., "Dopamine as a Prolactin (PRL) Inhibitor," Endocr. Rev. 22(6), pp. 724-763 (2001).
Breznik, R., et al., "Effectiveness of Antiestrogens in Infertile Men," Arch. Androl., vol. 31(1), pp. 43-48 (1993).
Check, J., et al., "Empirical Therapy of the Male with Clomiphene in Couples with Unexplained Infertility" Int. Journal Fertil., vol. 34(2), pp. 120-122 (1989).
Cooper, A., et al., "The Effects of Clomiphene in Impotence A Clinical and Endocrine Study," British Journal of Psychiatry, vol. 120, pp. 327-330 (1972).
Cunningham, G., et al., "Testosterone Replacement Therapy and Sleep-Related Erections in Hypogonadal Men," J. Clin. Endocrinol. Metab., vol. 70, No. 3, pp. 792-797 (1990).
Dangprasit, P., et al., "Development of Diclofenac Sodium Controlled Release Solid Dispersions by Spray Drying Using Optimization Strategy I. Powder Formulation," Drug. Devel. And Industrial Pharm. 21(20), pp. 2323-2337 (1995).
Davidson, J., et al., "Effects of Androgen on Sexual Behavior in Hypogonadal Men," J. Clin. Endocrinol. Metab., vol. 48, No. 6, pp. 955-958 (1979).
Ernst, S., et al., "Stereochemistry of Geometric Isomers of Clomiphene: A Correction of the Literature and a Reexamination of Structure-Activity Relationships," J. Pharmaceut. Sci., vol. 65, pp. 148-150 (1976).
Feldman, H., et al., "Age Trends in the Level of Serum Testosterone and Other Hormones in Middle-Aged Men: Longitudinal Results form the Massachusetts Male Aging Study," J Clin Endocrinol Metab. 87(2), pp. 589-598 (2002).
Fuse, H., et al., "Changes in Seminal Plasma Transferring Concentration Following Administration of Clomiphene Citrate," Archives of Andrology, vol. 31, pp. 139-145 (1993).
Guay, A., et al., "Effect of Raising Endogenous Testosterone Levels in Impotent Men with Secondary Hypogonadism: Double Blind Placebo-Controlled Trial with Clomiphene Citrate," Journal of Clinical Endocrinology and Metabolism, vol. 80, No. 12, pp. 3546-3552 (1995).
Guay, A., et al., "Possible Hypothalamic Impotence," Urology, vol. 38, No. 4, pp. 317-322 (1991).
Guay A., et al., "Results of Double Blinded Treatment With Clomiphene Citrate in Patients With Hypogoadotropic Hypogonadism," Annual Meeting of the Endocrine Society, Abstract No. 386, (Jun. 1993).
Hirshkowitz, M., et al., "Androgen and Sleep-Related Erections," J. Psychosomatic Research, vol. 42, No. 6, pp. 541-546 (1997).
Homonnai, Z., et al., "Clomiphene Citrate Treatment in Oligozoospermia: Comparison Between Two Regimens of Low-Dose Treatment," Fertlility and Sterility., vol. 60, No. 5, pp. 801-804 (1988).
Jarow, J., "Nonsurgical Treatment of Male Infertility: Empiric Therapy," Therapy, Chapter 23, pp. 410-422 (date of Publication Not Available).
Kharenko, A., et al., "Controlled Release From Oral Formulations Based on Interpolymeric Polymethacrylic Acid—Polyethylene Glycol Complex," Proceed. Intern. Symp. Control Rel. Bioact. Mater., vol. 22, pp. 232-233 (1995).
Matsumoto, A., et al., "Human Chorionic Gonadotropin and Testicular Function: Stimulation of Testosterone, Testosterone Precursors, and Sperm Production Despite High Estradiol Levels," Journal of Clinical Endocrinol. and Metab. vol. 56, No. 4, pp. 720-728 (1983).
Merck Index, 13th Ed., Entry 2410, p. 417 (2001).
Meshali, M., et al., "Effect of Interpolymer Complex Formation of Chitosan With Pectin or Acaxia on the Release Behaviour of Chlorpromazine HC1" Int. J. Phar., vol. 89, pp. 177-181 (1993).
Morales, A., et al., "Andropause: A Misnomer for a True Clinical Entity, " J. Urol., vol. 163, No. 3, pp. 705-712 (Mar. 2000) Abstract.
Purvis, K., et al., "Stability of Sperm Characteristics in Men with Disturbances in Sperm Quality," Int. Journal Androl., 12, pp. 171-178 (1989).
Soderguard, R., et al., "Calculation of Free and Bound Fractions of Testosterone and Estradiol-17β to Human Plasma Proteins at Body Temperature," J. Steroid Biochem, vol. 16, pp. 801-810 (1982).
Sternbach, et al., "Age-associated Testosterone Decline in Men: Clinical Issues for Psychiatry," Am. J. Psychiatry, vol. 155, No. 10, pp. 1310-1318 (1998) Abstract.
Suzuki, et al., "Endocrine Environment of Benign Prostatic Hyperplasia: Prostate Size and Volume are Correlated with Serum Estrogen Concentration," Scand. J. Urol. Nephrol., vol. 29, No. 1, pp. 65-68 (1995) Abstract.
Tenover, J., et al., "Serum Bioactive and Immunoreactive Follicle-Stimulating Hormone Levels and the Response to Clomiphene in Healthy Young and Elderly Men," Journal Clinical Endocrinol. and Metab., vol. 64, No. 6, pp. 1103-1108 (1987).
Tenover, J., et al., "The Effects of Aging in Normal Men on Bioavailable Testosterone and Luteinizing Hormone Secretion: Response to Clomiphene Citrate," Journal Clinical Endocrinol. Metab. , vol. 65, No. 6, pp. 1118-1126 (1987).
U.S. Pharmacopeia, United States Phamacopeia, 26$^{th}$ Ed., pp. 484-485 (2003).
Medical Information of Henan Province, "Report on 42 Cases of Treating Male Sterility with Clomiphene," vol. 2, No. 2 (Feb. 2001) (Translation).
Anonymous: "Zonagen Presents Data for Androxal in the Treatment of Hypogonadal Men and Data for Progenta as a Potential New Approach in the Treatment of Breast Cancer," News Release, The Healthcare Sales & Marketing Network, XP-002352050, Sep. 2, 2 2004.
Jiann, B., et al., "Effect of Clomiphene on $Ca^{2+}$ Movement in Human Prostate Cancer Cells," Life Sciences, vol. 70, No. 26, pp. 3167-3178 (May 2002).
PCT International Search Report of PCT/US2005/02500 dated Nov. 24, 2005.
PCT Written Opinion of PCT/US02/21524 dated Nov. 25, 2005.
Shida, K., et al., "Medical Treatment of Neoplasm with Steroids and Antisteroids," Chemical Abstracts Service, XP-002352053, May 12, 1984.
Singh, S., et al., "Changes in Fructose & Citric Acid in Accessory Glands of Reproduction of Rats Following Long-Term Treatment With Isomers of Clomiphene Citrate," Indian Journal of Experimental Biology, vol. 11, pp. 23-26 (Jan. 1973).
Wiehle, R.D., et al., "Androxal™ (oral enclomiphene citrate) Raises Free and Total Serum Testosterone in Hypogonadal Men: Comparison with Androgel 1 %®, " Fertility and Sterility, vol. 82, pp. 2004-2009, (2004).
Chang, C-F, et al., "Stimulation of Ovulation in Ayu, *Plecoglossus-altivelis*, by Treatment with Antiestrogens and Luteinizing Hormone-Releasing Hormone Analog," Aquaculture, vol. 101, Nos. 3-4, pp. 329-336 (1992).
Chakraborty, P. et al., "Effects of Long-Term Treatment With Estradiol or Clomiphene Citrate on Bone Mainteance, and Pituitary and Uterine Weights in Ovariectomized Rats," J. Steroid Biochem. Molec. Biol., vol. 40, No. 4-6, pp. 725-729 (1991).
Fitzpatrick, S., et al., "Effect of Estrogen Agonists and Antagonists on Induction of Progesterone Receptor in a Rat Hypothalamic Cell Line," Endocrinology, vol. 140, No. 9, pp. 3928-3937 (1999).
Haskell, S., "Selective Estrogen Receptor Modulators," Southern Medical Journal, vol. 96, No. 5, pp. 469-476 (2003).
Jimenez, M., et al., "Clomiphene Prevents Cancellous Bone Loss from Tibia of Ovariectomized Rats," vol. 138, No. 5, pp. 1794-1800 (1997).

(56) References Cited

OTHER PUBLICATIONS

Turner, R., et al., "Differential Responses of Estrogen Target Tissues in Rats Including Bone to Clomiphene, Enclomiphene, and Zuclomiphene," vol. 139, No. 9, pp. 3712-3720 (1998).
Young, R., et al., "A Short-Term Comparison of the Effects of Clomiphene Citrate and Conjugated Equine Estrogen in Menopausal/Castrate Women," Int. J. Fertil., vol. 36, No. 3, pp. 167-171 (1991).
Young, R., et al., "Qualitative Differences in Estrogenic/Antiestrogenic Effects of Clomiphene and Zuclomiphene," Int. J. Fertil., vol. 36, No. 5, pp. 291-295 (1991).
U.S. Appl. No. 11/750,190 Non-final office action dated Aug. 11, 2009.
U.S. Appl. No. 11/750,190 Notice of Allowance dated Jan. 8, 2010.
U.S. Appl. No. 11/571,150 Restriction Requirement dated Aug. 31, 2009.
U.S. Appl. No. 11/571,150 Non-final office action dated Oct. 14, 2009.
U.S. Appl. No. 11/997,858 Restriction Requirement dated Aug. 28, 2009.
U.S. Appl. No. 11/815,542 Restriction Requirement dated Aug. 31, 2009.
U.S. Appl. No. 11/815,542 Non-final office action dated Oct. 15, 2009.
Banner, A., et al., "Emerging Role of Corticosteroids in Chronic Obstructive Pulmonary Disease," The Lancet, vol. 354, pp. 440-441 (Aug. 7, 1999).
Casaburi, R., et al., "Effects of Testosterone and Resistance Training in Men with Chronic Obstructive Pulmonary Disease," American Journal of Respiratory and Critical Care Medicine, vol. 170, pp. 870-878 (2004).
Debigare, R., et al., "Peripheral Muscle Wasting in Chronic Obstructive Pulmonary Disease," American Journal of Respiratory and Critical Care Medicine, vol. 164, pp. 1712-1717 (2001).
International Search Report of PCT/US09/063621 dated Dec. 28, 2009.
Laghi, F., et al., "Respiratory and Skeletal Muscles in Hypogonadal Men with Chronic Obstructive Pulmonary Disease," American Journal of Respiratory and Critical Care Medicine, vol. 171, pp. 598-605 (2005).
PCT Written Opinion of PCT/US08/075433 dated Dec. 19, 2008.
PCT Written Opinion of PCT/US09/063621 dated Dec. 28, 2009.
Shanis, et al., Arch. Androl., vol. 21, pp. 109 (1991).
Sokel, Fertil and Steril, vol. 49, pp. 865 (1988).
Steiner, et al., "Antiestrogens and Selective Estrogen Receptor Modulators Reduce Prostte Cancer Risk," World J Urol., vol. 21, pp. 31-36 (2003).
Vippagunta, et al., Advanced Drug Delivery Reviews, vol. 48, pp. 3-26 (2001).
Grinenko, et al., Khimiko-farmatsevticheskii Zhurnal, vol. 23, No. 1, pp. 123-126 (1989).
PCT Written Opinion of PCT/US06/30053 dated Dec. 22, 2006.
Petak, S., et al., American Association of Clinical Endocrinologists Medical Guidelines for Clinlical Zpractice for the Evaulationand Treatment of Hypogonadism in Adult Male Patients, Endocrine Practice, vol. 8, pp. 439-456 (2002).
Ronnberg, "The Effect of Clomiphene Treatment on Different Sperm Parameters in Men with Idiopathic Oligozoospermia," Andrologia, vol. 12, No. 1, pp. 261-265 (1980).
Schultheiss, D., et al., "Testosterone Therapy in the Ageing Male: What About the Prostate?" Andrologia, vol. 36, No. 6, pp. 357-365 (2004).
Schweikert, et al., "Effects of Estrogen Deprivation on Human Benign Prostatic Hyperplasia," Steroid Biochem Mol Biol., vol. 44, No. 4-6, pp. 573-576 (1993).
Written Opinion of Singapore Patent Applc. 2007-05640-1 dated Aug. 13, 2008.
Stahl, F., et al., "Effects of Tamoxifen on the Levels of luteinizing Hormone (LH), Follicle Stimulating Hormone FSH), Prolactin (PRL), 17 beta-oestradiol (E2), and free dihydrotestosterone (DHT) in blood of patients with Benign Prostatic Hyperplasia," US National Library of Medicine, Bethesda, MD, US, vol. 82, No. 1, pp. 21-28 (1983).
Sterochemistry of Geometric Isomers of Clomiphene: A Correction of the Literature and a Reexamination of Structure-Activity Relationships, Journal of Pharmaceutical Science, vol. 65, No., pp. 184-150 (176) XP009056304, 1976.
Stedman's Medical Dictionary, William and Wilking, pp. 1312, 1439 & 1798-1799 (1995).
Tenover, J., et al., J Clin. Endocrine. Metabol., vol. 75, pp. 1092-1098 (1992).
Tenover, J., et al., "Male Hormone Replacement Therapy Including Andropause," Endrocrinology and Metabolism Clinics of North America, W.B. Saunders Company, Philadelphia, US, Dec. 1998, vol. 27, No. 4, pp. 969-987 XP008019800.
U.S. Appl. No. 10/427,768 Examiner's Interview Summary Record dated Nov. 19, 2007.
U.S. Appl. No. 10/427,768 Final office action dated Apr. 6, 2006.
U.S. Appl. No. 10/427,768 Non-final office action dated May 29, 2007.
U.S. Appl. No. 10/427,768 Non-final office action dated Oct. 12, 2005.
U.S. Appl. No. 10/427,768 Notice of Allowance and Examiner's Amendment dated Dec. 27, 2007.
U.S. Appl. No. 10/427,768 Restriction Requirement dated May 23, 2005.
U.S. Appl. No. 10/712,546 Non-final office action dated Mar. 15, 2006.
U.S. Appl. No. 10/712,546 Notice of Allowance dated Sep. 29, 2006.
U.S. Appl. No. 10/712,546 Restriction Requirement dated Nov. 10, 2005.
U.S. Appl. No. 11/570,190 Restriction Requirement dated Mar. 27, 2009.
90/008,024 Non-final office action dated Nov. 1, 2006.
Examiner Interview Summary Record dated Dec. 13, 2006.
90/008,024 Non-final office action dated Jan. 29, 2007.
90/008,024 Final office action dated Jun. 22, 2007.
90/008,024 Examiner Interview Summary Record dated Jul. 25, 2007.
90/008,024 Final office action dated Nov. 16, 2007.
90/008,024 Advisory Action dated Feb. 1, 2008.
90/008,024 Advisory Action dated Mar. 5, 2008.
90/008,024 Examiner's Answer dated Jun. 12, 2008.
90/006,921 Non-final office action dated Sep. 9, 2004.
90/006,921 Examiner's Interview Summary dated Oct. 20, 2004.
90/006,921 Final office action dated Feb. 23, 2005.
90/006,921 Petition Decision dated May 25, 2005.
90/006,921 Non-final office action dated Jun. 27, 2005.
Elanjian, Sona I., "Clomiphene for Male Infertility," Journal of Pharmacy Technology, vol. 12, No. 3, pp. 102-104 (1996).
Epstein, "Clomiphene Treatment in Oligospermic Infertile Males," Fertility and Sterility, vol. 28, No. 7, pp. 741-745 (1977).
Garg, Abhimanyu, "Medical progress: Acquired and Inherited Lipodystrophies," New England Journal of Medicine, vol. 35, No. 12, pp. 1231-1232 (2004).
Hayashi, Norio, et al., Hinyokika Kiyo (Acta Urologica Japonica), vol. 34, No. 5, pp. 847-850 (1988) with English translation.
Shirai, Takashi, et al., Saishin-Igaku (Latest Medical Science), vol. 45, No. 11, pp. 2250-2254 (1990) with English translation.
Sterochemistry of Geometric Isomers of Clomiphene: A Correction of the Literature and a Reexamination of Structure-Activity Relationships, Journal of Pharmaceutical Science, vol. 65, No., pp. 184-150 (1976) XP009056304.
Takihara, Hiroshi, Jin to Toseki (Kidney and Dialysis) vol. 41, Special Edition, pp. 759-761 (1996) with English translation.
Weissenberg, R., et al., "The Effect of Clomiphene Citrate and is Zu or En isomers on the Reproductive System of the Immatuyre Male Rate," Andrologia, vol. 24, pp. 161-165 (19992).
Written Opinion of Singapore Patent Applc. 2007-05640-1 dated Jul. 9, 2008.
ACCE Clinical Practice Guidelines for the Evaluation and Treatment of Hypogonadism in Adult Male Patients (1996).

(56) References Cited

OTHER PUBLICATIONS

Agarwal, et al., "Male Sexual Dysfunction After Stroke," J Assoc. Physicians India, vol. 37, No. 8, pp. 505-507 (1989).
Barg, P., et al., "Male Factor: Clinical Evaluation of the Semen Analysis," Infert. Reprod. Med. Clin. North Amer., vol. 2, pp. 333-340 (1991).
Bartsch, G., "The Effect of Antiestrogen, Antiandrogen, and the Prolactin Inhibitor 2 Bromo-'alpha!-ergocriptine on the Stromal Tissue of Human Benign Prostatic Hyperplasia. Correlation of Sterological Data and Plasma Hormones," Database Embase; Elsevier Science Publishers, Amsterdam, NL, 1981, vol. 18, No. 4, pp. 308-312.
Bhasin, S., et al., J. Clin Endocrin, Metabol., vol. 91, pp. 1995-2010 (2006).
Brody, J., "Sperm Found Especially Vulnerable to Enviroment," The New York Times, Mar. 10, 1981.
Broulik, P.D., "Tamoxifen Prevents Bone Loss in Castrated Male Mice," Hormone and Metabolic Research, Thieme-Stratton, Stuttgart, DE, vol. 32, No. 5, pp. 181-184 (2002) XP009041862.
Burghardt, et al., "Gap Junction Modulation in Rat Uterus. III. Structure-Activity Relationships of Estrogen Receptor-Binding Ligands on Myometrial and Serosal Cells," Biol. Reprod. vol. 36, No. 3, pp. 741-751 (1977).
Drew, A., "Letter: Possible Teratogenic Effect of Clomiphene," Developmental Medicine and Child Neurology, vol. 16, No. 2, pp. 276 (1974).
Editions Du Vidal Ed—Editions Du Vidal: Vidal 1997; Dictionnaire Vidal 1997, Paris, FR, p. 1161 XP002150196.
Eil, "Ketoconazole Binds to the Human Androgen Receptor," Horm Metab Res., vol. 24, No. 8, pp. 367-370 (1992).
EP Supplementary Search Report of EP 02748104 dated Jun. 24, 2005.
EP Supplementary Search Report of EP 06720243 dated Aug. 6, 2008.
EP Supplementary Search Report of EP 06738985 dated Aug. 15, 2008.
EP Supplementary Search Report of EP 06800648 dated Jul. 21, 2008.
Excerpt on www.medscape.com from Drug Ther. Perspect., vol. 10, pp. 1-5 (1997).
Glasier, A., et al., "A Comparison of the Effects on Follicular Development Between Clomiphene Citrate Its Two Separate Isomers and Spontaneous Cycles," Human Reproduction, vol. 4, No. 3, pp. 252-256 (1989).
Guay, A., et al., Internatl. J. Ompot. Res., vol. 15, pp. 156-165 (2003).
Guzick, D., et al., "Sperm Morphology, Motility and Concentration in Fertile and Infertile Men," N. Engl. J. Med., vol. 345, pp. 1388-1393 (2001).
Hanus, M., et al., "Antiestrogens (Tamoxifen) in the Alternative Therapy of Benign Prostatic Hyperplasial," US National Library of Medicine, Bethesda, MD, Database Medline, vol. 72, No. 7, pp. 316-318 (1993).
Herzog, A. G., "Reproductive Endocrine Considerations and Hormonal Therapy for Men with Epilepsy," Epilepsia, Raven Press Ltd., New York, US (1991), vol. 32, No. Suppl. 6, pp. S34-S37.
International Preliminary Examination Report of PCT/US02/21524 dated Mar. 3, 2006.
International Preliminary Report on Patentability of PCT/US05/02500 dated Jan. 16, 2007.
International Preliminary Report on Patentability of PCT/US06/003882 dated Aug. 7, 2007.
International Preliminary Report on Patentability of PCT/US06/030053 dated Feb. 5, 2008.
International Preliminary Report on Patentability of PCT/US06/10022 dated Sep. 25, 2007.
International Search Report of PCT/US08/075433 dated Dec. 19, 2008.
International Search Report of PCT/US02/21524 dated Jun. 18, 2003.
International Search Report of PCT/US06/003882 dated Aug. 14, 2006.
International Search Report of PCT/US06/10022 dated Jan. 10, 2007.
International Search Report of PCT/US06/30053 dated Dec. 22, 2006.
Jones, T. Hugh., "Testosterone Associations with Erectile Dysfunction, Diabetes, and the Metabolic Syndrome," European Urology Supplements, vol. 6, pp. 847-857 (2007).
Kadioglu, et al., Treatment of Idiopathic and Postvaricocelectomy Oligozoospermia with Oral Tamoxifen Citrate, BJU Int., vol. 83, No. 6, pp. 646-648 (1999).
Ke, H. Zhu, et al., "Lasofoxifene (CP-336,156), A Selective Estrogen Receptor Modulator, Prevents Bone Loss Induced by Aging and Orchidectomy in the Adult Rat," Endocrinology, vol. 141, No. 4, pp. 1338-1344 (2000) XP001170303.
Kidd, S., et al., "Effects of male age on semen quality and fertility: A review of the literature," Fertility and Sterility, vol. 75, pp. 237-248 (2001).
Kotoulas, et al., "Tamoxifen Treatment in Male Infertility. I. Effect on spermatozoa," Fertil. Steril., vol. 61, No. 5, pp. 911-914 (1994).
Lewis, B., et al., "Medical Implication of the Biological Clock," JAMA, vol. 296, pp. 2369-2371 (2006).
Lim, V., et al., "Restoration of Plasma Testosterone Levels in Uremic Men with Clomiphene Citrate," Journal of Clinical Endocrinology and Metabolism, New York, US vol. 43, No. 6, pp. 1370-1377 (1976) XP 009041861.
Lund, et al., "Testosterone and Andropause: The Feasibility of Testosterone Replacement Therapy in Elderly Men," Pharmacotherapy, vol. 19, No. 8, pp. 951-956 (1999).
Macleod, J., et al., J. Urology, vol. 66, pp. 436-449 (1951).
McKinlay, et al., "The Questionable Physiologic and Epidemiologic Basis for a Male Climacteric Syndrome: Preliminary Results from the Massachusetts Male Aging Study," Maturitas, vol. 11, No. 2, pp. 103-115 (1989).
Parini, et al., "Importance of Estrogen Receptors in Hepatic LDL Receptor Regulation," Ateriosclerosis, Thrombosis, and Vascular Biology, vol. 17, pp. 1800-1805 (1997).
PCT Written Opinion of PCT/US05/02500 dated Sep. 14, 2006.
PCT Written Opinion of PCT/US06/003882 dated Aug. 4, 2007.
PCT Written Opinion of PCT/US06/030053 dated Feb. 5, 2008.
PCT Written Opinion of PCT/US06/10022 dated Jan. 10, 2007.
Adashi, Eli, Y., "Clomiphene Citrate: The Case for a Monoisomeric Preparation," Bailliere's Clinical Obstetrics and Gynaecology, vol. 7, No. 2, pp. 331-347 (Jun. 1993).
Bandhauer, K., et al., "Varicocele: Spermiogram, Testicular Biopsy, Plasma Testosterone, Results of Therapy," Urologe—Ausgabe A 1977 DE, vol. 16, No. 3, pp. 154-157 (1977).
Baumann, R. J., et al., "Clomiphene Analogs with Activity In Vitro and In Vivo Against Human Breast Cancer Cells," Biochemical Pharmacology, vol. 55, pp. 841-851 (1998).
Clark, James H., et al., "Agonistic and Antagonistic Effects of Clomiphene Citrate and Its Isomers," Biology of Reproduction, vol. 25, pp. 667-672 (1981).
Clomid Information Sheet (available online at http//clomid.us) accessed Mar. 2, 2011.
EP Extended Search Report for EP 11153365.9 dated Jan. 20, 2012.
Anonymous: Ferring Arzneimittel: "Clomifen Ferring 50 mg Tabletten," (http://www.fachinfo.de/data/fi/jsearch?wirkstoff retrieved on May 31, 2011) pp. 1-5 (XP007918978) Oct. 1, 2010.
Ganchev, B., et al., "Quantification of Clomiphene Metabolite Isomers in Human Plasma by Rapid-Resolution Liquid Chromatography-Electrospray Ionization-Tandem Mass Spectrometry," Anal. Bioannal. Chem., vol. 400, pp. 3429-3441 (2011).
International Preliminary Report on Patentability of PCT/US2009/063621 dated May 19, 2011.
International Search Report and Written Opinion of PCT/US2013/028356 dated Apr. 16, 2013.
International Search Report and Written Opinion of PCT/US13/032659 dated Jul. 19, 2013.
International Search Report and Written Opinion of PCTUS2013/026178 dated Jul. 22, 2013.
International Search Report and Written Opinion of PCT/US2012/049451 dated Oct. 11, 2012.

(56) References Cited

OTHER PUBLICATIONS

Macrochem Press Release (Opeterone Topical Testosterone Cream, accessed online Sep. 20, 2010).

Makhsida, N., et al., "Hypogonadism and Metabolic Syndrome: Implications for Testosterone Therapy," J. Urology, vol. 174, pp. 827-834 (2005).

Mikkelson, T., et al., "Single-Dose Pharmacokinetics of Clomiphene Citrate in Normal Volunteers," Fertility and Sterility, vol. 46, No. 3, pp. 392-396 (1986).

Ruenitz, Peter, et al., "Phenolic Metabolites of Clomiphene: [(E,Z)-2-[4-(1,2,Diphenyl-2-chlorovinyl)phenoxy]ethyl] diethylamine. Preparation, Electrophilicity, and Effects in MCF 7 Breast Cancer Cells," J. Med. Chem., vol. 32, pp. 192-197 (1989).

Sankaran M.S., et al., "Effects of Progesterone, Oestradiol and or Clomiphene on Liver Glycogen and Blood Glucose in Intact and Adrenalectomised Rats During Delayed Implantation," ACTA Endocrinologica, vol. 76, pp. 678-688 (1974).

Tan, R.S., et al., "An Unusual Case of Vascular Hypogonadism Treated with Clomiphene Citrate and Testosterone Replacement," Andrologia, vol. 41, No. 1, pp. 63-65 (Feb. 1, 2009).

Virginia Mason Medical Center (available online at www.virginiamason.org) accessed Mar. 2, 2011.

Williams, D., et al., Foye's Principles of Medicinal Chemistry 5 Edition, Part I/Principles of Drug Discovery, Lippincott Williams & Wilkins, p. 50 (2002).

Young S., "Serum Concentrations of Enclomiphene and Zuclomiphene Across Consecutive Cycles of Clomiphene Citrate Therapy in Anovulatory Infertile Women," Fertility and Sterility, vol. 71, No. 4, pp. 639-644 (1999).

U.S. Appl. No. 12/205,456 Restriction Requirement dated Apr. 30, 2010.
U.S. Appl. No. 12/205,456 Non-Final Office Action dated Sep. 28, 2010.
U.S. Appl. No. 12/205,456 Final Office Action dated Mar. 7, 2011.
U.S. Control No. 90/008,024 Decision on Appeal dated Aug. 28, 2009.
U.S. Appl. No. 12/205,456 Non-Final Office Action dated Apr. 24, 2012.
U.S. Appl. No. 12/205,456 Notice of Allowance dated Oct. 15, 2012.
U.S. Appl. No. 13/590,045 Non-Final Office Action dated Oct. 9, 2012.
U.S. Appl. No. 10/483,458 Notice of Allowance dated Apr. 21, 2010.
U.S. Appl. No. 10/483,458 Final Office dated Mar. 17, 2010.
U.S. Appl. No. 10/483,458 Non-final office action dated Jul. 20, 2009.
U.S. Appl. No. 10/483,458 Advisory Action dated Jan. 16, 2009.
U.S. Appl. No. 10/483,458 Final office action dated Nov. 19, 2008.
U.S. Appl. No. 10/483,458 Non-final office action dated Feb. 13, 2008.
U.S. Appl. No. 10/483,458 Restriction Requirement dated Oct. 25, 2007.
U.S. Appl. No. 11/750,190 Notice of Allowance dated Feb. 5, 2010.
U.S. Appl. No. 11/815,542 Final Office action dated Mar. 30, 2010.
U.S. Appl. No. 11/815,542 Advisory Action dated Jun. 16, 2010.
U.S. Appl. No. 11/815,542 Non-final office action dated May 10, 2011.
U.S. Appl. No. 11/815,542 Final Office action dated Nov. 15, 2011.
U.S. Appl. No. 11/815,542 Non-Final Office Action dated Feb. 28, 2012.
U.S. Appl. No. 11/815,542 Notice of Allowance dated Apr. 18, 2012.
U.S. Appl. No. 11/814,068 Non-final office action dated Apr. 12, 2011.
U.S. Appl. No. 13/196,688 Notice of Allowance dated Oct. 16, 2012.
U.S. Control No. 90/008,024 Decision on Request for Rehearing dated Aug. 2, 2010.

\* cited by examiner

METHODS AND MATERIALS FOR THE TREATMENT OF TESTOSTERONE DEFICIENCY IN MEN

CROSS-REFERENCE TO RELATED APPLICATIONS

This application is a divisional of U.S. application Ser. No. 10/483,458, filed Jul. 2, 2005, now U.S. Pat. No. 7,759,360, which is the U.S. National Stage of International Application No. PCT/US02/21524, filed Jul. 9, 2002, and which claims the benefit of U.S. Provisional Patent Application No. 60/304,313, filed on Jul. 9, 2001, the contents of each of which is incorporated herein by reference in its entirety.

FIELD OF THE INVENTION

The present invention relates to the compositions and methods for increasing testosterone levels. More specifically, the present invention relates to a composition comprising clomiphene enriched for trans-clomiphene. The present invention also relates to the use of a composition comprising clomiphene enriched for trans-clomiphene reagents for increasing testosterone levels.

BACKGROUND

Testosterone is the primary male androgen, playing a vital role in overall male health. Testosterone is essential to the development and maintenance of specific reproductive tissues (testes, prostate, epididymis, seminal vesicle, and penis) and male secondary sex characteristics. It plays a key role in libido and erectile function and is necessary for the initiation and maintenance of spermatogenesis. Testosterone also has important functions not related to reproductive tissues. For example, it positively affects body composition by increasing nitrogen retention, which supports lean body mass, muscle size and strength. If also acts on bone to stimulate bone formation.

Testosterone secretion is the end product of a series of hormonal processes. Gonadotropin-releasing hormone (GnRH), which is secreted in the hypothalamus, controls the pulsatile secretion of luteinizing hormone (LH) and follicle stimulating hormone (FSH), which are secreted by the anterior pituitary. LH, in turn, regulates the production and secretion of testosterone in the Leydig cells of the testes, while FSH assists in inducing spermatogenesis.

Testosterone is most often measured as "total testosterone." This measurement includes testosterone that is bound to sex hormone-binding globulin (SHBG) (~44%) and is therefore not bioavailable and testosterone which either is free (~2%) or loosely bound to other proteins (non-SHBG-bound) (~54%).

Results from a WHO study indicate that testosterone is normally secreted in a circadian rhythm, with higher levels in the morning and nadir levels occurring around 8 to 10 p.m. See FIG. 1. This variation in testosterone secretion throughout the day becomes much less pronounced in older men (mean age equals 71 years). The importance of this rhythm is not known at this time.

Samples were obtained from both young and elderly patients every 10 minutes for 24 hours via an indwelling cannula. According to Tenover (1987) the mean 24 hr total serum testosterone levels in healthy young men (age range 22 yrs.-35 yrs. mean 27.3 yrs) was 4.9±0.3 (±SEM) mg/ml (17.0 nmol/L) while older men (age range 65 yrs-84 yrs. mean 70.7 yrs.) had a significantly lower mean 24 hrs. total serum testosterone level of 4.1±0.4 mg/ml. (P<0.5; 14.2 nmol/L).

Total serum testosterone levels obtained from single random samples were also significantly lower in older men (4.0±0.2 mg/ml [13.9 nmol/L]) as compared to 4.8±0.2 mg/ml [16.6 nmol/L] in healthy young men.

Testosterone deficiency can result from underlying disease or genetic disorders and is also frequently a complication of aging. For example, primary hypogonadism results from primary testicular failure. In this situation, testosterone levels are low and levels of pituitary gonadotropins (LH and FSH) are elevated. Secondary hypogonadism is due to inadequate secretion of the pituitary gonadotropins. In addition to a low testosterone level, LH and FSH levels are low or low-normal. Some of the sequelae of adult testosterone deficiency include a wide variety of symptoms including: loss of libido, erectile dysfunction, oligospermia or azoospermia, absence or regression of secondary sexual characteristics, progressive decrease in muscle mass, fatigue, depressed mood and increased risk of osteoporosis.

Several forms of testosterone therapy exists in the United States today. Recently, transdermal preparations have gained favor in the market. However, a scrotal testosterone patch results in supraphysiologic levels of 5α-dihydrotestosterone (DHT) due to the high concentration of 5α-reductase in scrotal skin. It is not known whether these elevated DHT levels have any long-term health consequences. Nonscrotal systems are considered more convenient and most patients achieve average serum concentrations within the normal range and have normal levels of DHT. Oral testosterone therapy is not recommended because doses required for replacement therapy are associated with significant risk of hepatotoxicity.

SUMMARY

The present invention is directed to compositions useful for increasing testosterone levels in male mammals and for ameliorating or preventing the sequelae of low testosterone levels. In one of its aspects the invention is directed to compositions having active ingredients comprising 0% to 29% weight/weight of (cis, -Z-, trans-clomiphene) (hereinafter "cis-clomiphene") and 100% to 71% w/w (trans-, E-, cis-clomiphene) (hereinafter "trans-clomiphene") or pharmaceutically acceptable salts thereof. Among the preferred compositions of the present invention which contain both cis-clomiphene and trans-clomiphene are compositions wherein the ratio of trans-clomiphene and cis-clomiphene is greater than 71/29. A more preferred composition according to the present invention comprises about 100% w/w of active ingredients of trans-clomiphene or a pharmaceutically acceptable salt thereof. All compositions of the present invention may further comprise suitable pharmaceutical excipients diluents, carriers, and the like. Analogs of the cis-clomiphene and trans-clomiphene are also contemplated for use in all aspects of the present invention.

The present invention is also directed to methods for increasing serum testosterone levels in hypogonadal male mammals (and for ameliorating or preventing the sequelae of low testosterone levels), the method comprising administering to a subject male an effective amount of a composition according to the present invention, the compositions having active ingredients comprising 0% to 29% weight/weight of cis-clomiphene and 100% to 71% w/w trans-clomiphene including any of their pharmaceutically acceptable salts thereof. Among the preferred methods are those in which the administered compositions contain both isomers wherein the ratio of trans-clomiphene to cis-clomiphene is greater than 71/29. A more preferred method comprises administering to the male a composition comprising about 100% w/w of trans-clomiphene.

DETAILED DESCRIPTION

The present invention provides methods and compositions useful for increasing testosterone levels in male mammals and for ameliorating or preventing the sequelae of low testosterone levels including but not limited to those described above.

Figure 2:
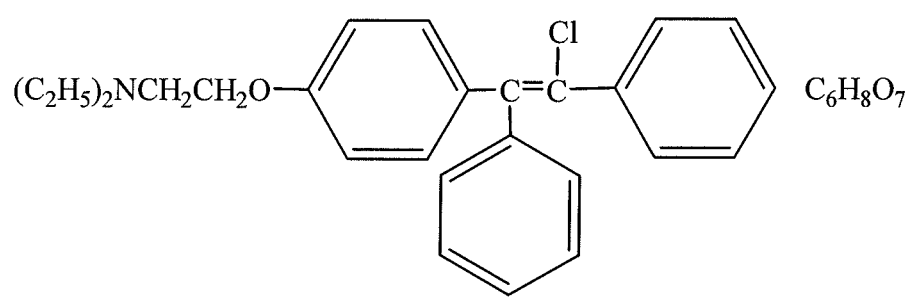
FIG. 2 shows the chemical structure of clomiphene citrate.

Clomiphene (FIG. 2) is an antiestrogen related to tamoxifen that blocks the normal estrogen feedback on the hypothalamus and subsequent negative feedback on the pituitary. This leads to increases in luteinizing hormone (LH) and follicle stimulating hormone (FSH). In men, these increased levels of gonadotropins stimulate the Leydig cells of the testes and result in the production of higher testosterone levels. Clomiphene citrate has the following structure:

Ernst et al., J. Pharmaceut. Sci. 65:148 (1976), have shown that clomiphene is a mixture of two geometric isomers which they refer to as cis, -Z-, clomiphene (cis-clomiphene or zuclomiphene) and trans-, E-, clomiphene, (trans-clomiphene or enclomiphene). According to Ernst, et al. trans-clomiphene HCI has a melting point of 149° C.-150.5° C., while cis-clomiphene HCI has a melting point of 156.5° C.-158° C.

Ernst et al. have also noted that (the trans-isomer) is anti-estrogenic (AE) while the cis-isomer is the more potent and more estrogenic form and has also been reported to have anti-estrogenic activity. The authors attribute the effect of the drug on ovulatory activity to both forms stating that the mixture is more effective than trans-clomiphene alone. The trans-isomer aids ovulation at the level of the hypothalamus. The estrogenic isomer cis-clomiphene contributes to enchanced ovulation elsewhere in the physiologic pathway leading to ovulation. The isomers are also reported to have different in vivo half-life. Furthermore the cis form has been reported to leave residual blood levels for in excess of one month following a single dose.

Vandekerckhove, et al. (Cochrane Database Syst Rev 2000; (2):CD000151 (2000)) noted that ten studies involving 738 men have suggested that anti-estrogens appear to have a beneficial effect on endocrinal outcomes, i.e. testosterone, but there is not enough evidence to evaluate fertility effects. Nevertheless should clomiphene administration enhance testosterone levels then one could easily conclude that the drug should positively impact the side effects of testosterone deprivation as long as the testes still retain the ability to respond to gonadotropin stimulation.

Clomiphene is currently approved as a mixture of both cis- and trans-isomers, the cis-isomer being present as about 30% to 50% (Merck Manual) for fertility enhancement in the anovulatory patient. Clomiphene improves ovulation by initiating a series of endocrine events culminating in a preovulatory gonadotropin surge and subsequent follicular rupture. The drug is recommended to be administered for 5 days at a dose of up to 100 mg daily. Clomiphene has also been associated with numerous side effects including: blurred vision, abdominal discomfort, gynecomastia, testicular tumors, vasomotor flushes, nausea, and headaches. Furthermore, other studies suggest that clomiphene possesses both genotoxic and tumor enhancement effects. The net outcome of these observations is that clomiphene in its current format, having between 30% and 50% of the cis isomer, would be unacceptable for chronic therapy in men for the treatment of testosterone deficiency.

Clomiphene has also been used for therapeutic intervention in men with low testosterone levels. Tenover et al., J. Clin. Endocrinol. Metab. 64:1103, (1987) and Tenover et al., J. Clin. Endocrinol. Metab. 64:1118 (1987) found increased in FSH, LH in both young and old men after treatment with clomiphene. They also found increases in free and total testosterone in men with young men showing significant increases Studies were also conducted to determine whether or not clomiphene could be used to improve fertility in men by improving semen quality. Homonnai et al. Fertil. and Steril 50:801 (1988) saw increases in sperm concentration and count but others have not. (See e.g., Sokel, et al., Fertil. and Steril. 49:865 (1988); Check, et al., Int. J. Fertil. 34:120 (1989); Purvis, et al., Int. J. Androl 21:109 (1989); and Breznik, Arch. Androl. 21:109 (1993).) One group saw a deterioration in the percentage of normal sperm with long-term treatment. Shamis, et al., Arch. Androl 21:109 (1991). A WHO study showed no changes in semen quality or fertility after 6 months of treatment (Anonymous Androl. 15:299 (1992).) A meta-analysis seems to confirm that testosterone levels go up in men with poor quality sperm but not fertility. (Vanderkerckhove, et al., 2000). Studies have also suggested that long term treatment with clomiphene does not seem to have a drastic deleterious effect on health, although it did show that treatment resulted in poorer sperm quality after 4 months. Studies have kept men on clomiphene for as long as 18 months and at levels of 25 mg per day or 100 mg every other day.

In 1991, Guay et al (Urology 38:377 (1991)) suggested that clomiphene could treat sexual dysfunction in men. Their hypothesis seems to be that sexual function follows testosterone levels. This was supported by early studies showing positive influence of androgens and sexual function, Davidson, et al., J. Clin. Endocrinol. Metab. 48:955 (1979), and studies that rated sleep-related erections as a strong response to T, Cunningham, et al., J. Clin. Endocrinol. Metab. 70:792 (1990). However, in 1995, Guay et al. (Gray, et al., J. Clin. Endocrinol. Metab. 80:3546 (1995)) published a study in which they saw increase in LH, FSH, and testosterone after 2 months of clomiphene but no effects on erectile dysfunction. There might be some advantage for young men and specific groups of older men, but it seems that just raising the testosterone level is not enough. Effects of testosterone on sleep-related erections may have been taken too seriously (Herskowitz, et al., J. Psychosomat. Res. 42:541 (1997)).

According to the present invention, a composition comprising of one isomer preferably trans-clomiphene or a pre-defined blend of the isomers of clomiphene as described below differing from the normally produced mixture are used to enhance testosterone levels while reducing the side effects of the drug. Thus, the present invention provides an oral therapy for increasing testosterone levels, which lacks or has diminished side effects connected with the existing clomiphene formulations.

In one embodiment of the present invention, a patient who has a need or desire to increase their serum testosterone levels are administered one or more dosages of an effective amount of composition comprising trans-clomiphene at a dosage between one mg to about 200 mg (although the determination of optimal dosages is with the level of ordinary skill in the art). Cis-clomiphene may also be present in the composition so long as the ratio of trans-clomiphene to cis-clomiphene is greater than 71/29. Analogs of the trans- and cis-isomers of clomiphene such as those described in Ernst, et al. supra are also useful in the practice of the present invention.

Figure 1:
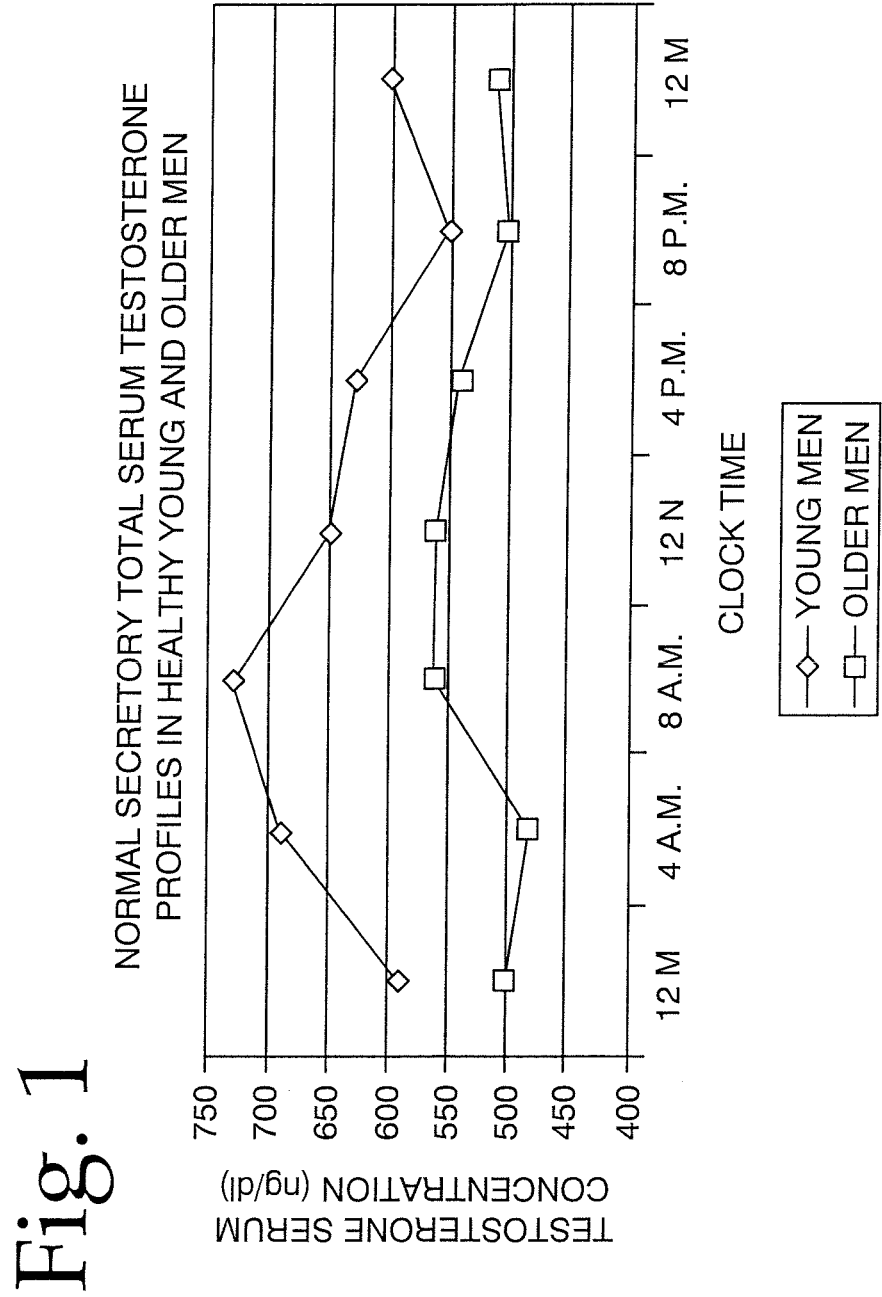
FIG. 1 is a graphic representative of the normal secretory total serum testosterone profiles in healthy men (young and old).

Dosages are preferably (but not necessarily) administered as part of a dosage regimen designed to give rise to serum testosterone levels that mimic or correspond to the normal secretary total serum testosterone profile described in FIG. 1. For example, according to FIG. 1 a dosage of the preferred composition may be administered in a pharmaceutical formulation that would give rise to peak serum testosterone levels at around 8 a.m. Such pharmaceutical formulations may be in the form of sustained release formulations prepared as described for example in U.S. Pat. No. 6,221,399, Japanese patent 4-312522, Meshali et al, Int. J. Phar. 89:177-181 (1993), Kharenko et al, Intern. Symp. Control Rel. Bioact. Mater. 22:232-233 (1995), WO 95/35093, Dangprasit et al, Drug. Devel. and Incl. Pharm. 21 (20):2323-2337 (1995); U.S. Pat. Nos. 6,143,353, 6,190,591, 6,096,338, 6,129,933, 6,126,969, 6,248,363 and other sustained release formulations well known in the art.

Suitable pharmaceutical compositions or unit dosage form may be in the form of solids, such as tablets or filled capsules or liquids such as solutions suspensions, emulsions, elixirs or capsules filled with the same, all for oral use. The compositions may also be in the form of sterile injectable solutions or emulsions for parenteral (including subcutaneous) use. Such pharmaceutical compositions and unit dosage forms thereof may comprise ingredients in conventional proportions.

Compositions according to the present invention may also be administered by the intravenous, subcutaneous, buccal, transmucusal, intrathecal, intradermal, intracisternal or other routes of administration. After administration of the composition serum testosterone levels may be measured as described above and dosages may be altered to achieve a sufficient increase in the serum testosterone levels to achieve the desired physiological results associated with normal testosterone described above.

All of the references discussed herein are incorporated by reference in their entirety.

The following Example is meant to be illustrative of the invention and is not intended to limit the scope of the invention as set out is the appended claims.

EXAMPLE 1

Effects of Clomids on Serum Testosterone in Male Baboons

Adult, male, Baboons were given 1.5 mg/kg of Clomid, Enclomid (trans-Clomid) or Zuclomid (cis-Clomid) for 12 consecutive days. The samples analyzed were sera taken on the day of first treatment before being given test article (day 0), after 12 days of treatment (day 12) and 7 days after the last treatment (end or wash-out).

1. Effects on Body Weight and Serum LH, FSH, PRL and Testosterone

Figure 3:
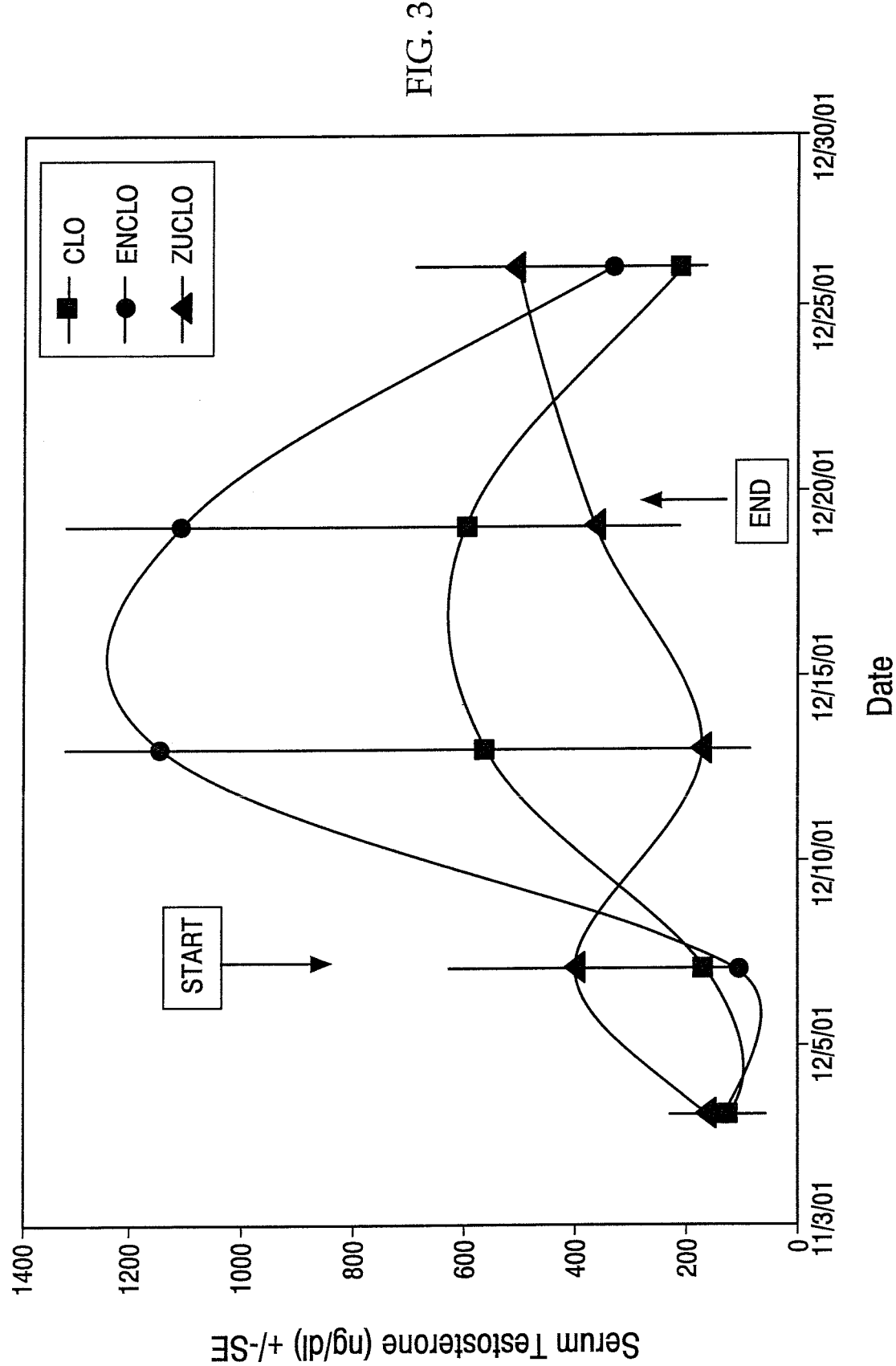
FIG. 3 is a graphic demonstration of the time course of serum testosterone levels with Clomid, Enclomid and Zuclomid.

There were significant increases in total serum testosterone in the group receiving Enclomid. See Table 1. There were no differences among groups in the baseline period or at day 0. There were also no differences among the three groups 7 days after treatment (the washout period). However, Enclomid produced higher levels of testosterone compared to Clomid and Zuclomid on day 6 ($p=0.03$ and $p=0.00002$ respectively) and compared to Zuclomid on day 12 ($p=0.047$). Zuclomid clearly did not raise total serum testosterone to any extent. Compared to the animals receiving Enclomid, the animals receiving Clomid exhibited more variable total testosterone levels on day 6 and later as judged by their coefficients of variations. When we looked at the time course of the effects (FIG. 3), we determined that only Enclomid significantly and statistically raised total serum testosterone on days 6 and 12 compared with either baseline or day 0 values. Moreover, cessation of Enclomid treatment, resulted in a significant drop in the level of total serum testosterone between day 12 and day 18 (washout). This indicates that Enclomid is readily cleared from the circulation consistent with the metabolic clearance seen for Enclomid in humans. Enclomid was clearly better and more consistent than Clomid itself and Zuclomid was ineffective.

TABLE 1

Serum Testosterone Levels (ng/dl)

| Group | ID | baseline Dec. 3, 2001 | 0 day Dec. 7, 2001 | 6 days Dec. 13, 2001 | 12 days Dec. 20, 2001 | wash-out Dec. 26, 2001 |
|---|---|---|---|---|---|---|
| CLO | 7500 | 79.01 | 76.15 | 940.97 | 891.5 | 150.9 |
|  | 9012 | 97.55 | 305.24 | 585.92 | 555.6 | 316.3 |
|  | 9097 | 158.06 | 102.94 | 151.12 | 318.9 | 143.6 |
|  | mean | 111.5 | 161.4 | 559.3 | 588.7 | 203.6 |
|  | SD | 41.3 | 125.2 | 395.6 | 287.7 | 97.7 |
| ENCLO | 7223 | 64.57 | 74.96 | 1223.8 | 633.6 | 307.2 |
|  | 8021 | 166.86 | 133.59 | 1128.2 | 1466 | 399.2 |
|  | 8369 | 170.45 | 106.47 | 1081.1 | 1166 | 271 |
|  | mean | 134.0 | 105.0 | 1144.4 | 1088.5 | 325.8 |
|  | SD | 60.1 | 29.3 | 72.7 | 421.6 | 66.1 |
| ZUCLO | 7438 | 124.84 | 210.4 | 137.51 | 314.5 | 359.7 |
|  | 8292 | 104.66 | 67.37 | 169.98 | 406.1 | 860.5 |
|  | 10098 | 282.29 | 904.82 | 227.95 | 353.0 | 274.1 |
|  | mean | 170.6 | 394.2 | 178.5 | 357.9 | 498.1 |
|  | SD | 97.3 | 448.0 | 45.8 | 46.0 | 316.8 |
|  | ANOVA | $p = 0.61$ | $p = 0.43$ | $p = 0.007$ | $p = 0.57$ | $p = 0.256$ |
|  | K-W | $p = 0.56$ | $p = 0.84$ | $p = 0.051$ | $p = 0.079$ | $p = 0.252$ |

There were no changes in serum LH or FSH. The ratio of total serum testosterone to LH followed the same pattern as total serum testosterone, suggesting a lack of dependence (data not shown). There was also no change in body weight during the 12 day study. There was a decrease in serum prolactin (PRL) during the study in the group receiving Enclomid, suggesting an effect of antiestrogen that has been described in part (Ben-Jonathan and Hnasko, 2001) and expected on the basis of the fact that as men age, testosterone declines and Prolactin increase (Feldman et al., 2002).

2. Effects on Clinical Chemistry Parameters

The mean values for each parameter did not differ among the three groups for any test parameter at the beginning of the study as determined by ANOVA or by the Kruskal-Wallis test.

All groups exhibited normal values at each parameter except for (1) serum sodium; a related calculated parameter, anionic gap, which were low for all nine baboons throughout the trial; (2) serum glucose; and (3) BUN which were high on day 0 for the group which would be treated with Enclomid. On day 12 of treatment and 7 days after treatment (washout), there were no differences among groups for any parameter except anionic gap that showed that the Clomid and Zuclomid groups had lower values than the Enclomid group. The values of serum sodium and anionic gap appear to be anomalies associated with this group of baboons.

There were substantive effects on the red blood cell population with Enclomid and Zuclomid and on hematocrit with Zuclomid. All the compounds lower the mean cell hemoglobin concentration (MCHC) either at day 0 or at the endpoint. With no change in mean cell hemoglobin (MCH) and an increase in the mean cell volume (MCV), the lowering of MCHC is predictable. Although testosterone might be expected to raise hematocrit, only Zuclomid treatment, which did not increase total serum testosterone, demonstrated a statistical difference. Clearly, men in a clinical trial that uses Zuclomid should be monitored for the characteristics of their red blood cell population. Enclomid would be predicted to have less of an effect.

There appears to be a clear effect of 12-day Enclomid treatment on platelets although the values found stayed within the normal range. One thing to consider here is the sexual dimorphism in platelet counts between male and female baboons (279 for males vs. 348 for females). This is likely to be due to hormones. Since the Enclomid group demonstrated increased testosterone, the lowering of the platelet count could be secondary to the change in testosterone in this group. Moreover, treatment with Enclomid pushed the platelet count to its normal male level from a day 0 level that was the high end of the normal range for this group. Enclomid would not necessarily predict a deleterious effect on platelets.

All the Clomids tested had effects on the white blood cell (WBC) population, the most striking was that of Enclomid on raising the counts of lymphocytes and eosinophiles. The effects are not as straightforward as they would seem to be. There appears to be a strong effect of Enclonud on lowering the percent of granulocytes in the blood. The effects are very strong after the 7-day washout period when the values are decreased below the normal range. (This time course could reflect the relatively long time required to affect change the WBC population.) There is little sexual dimorphism in baboons with respect to the white blood cell populations, so the effects are more likely to be due to the compound itself than changes in testosterone. However, when we look at the calculated count of granulocytes using the WBC count, we find no differences in granulocyte count due to any compound. Concomitantly, it is the lymphocyte story that is the most interesting. Both the count and percent lymphocytes in the population increase with Enclomid treatment. Whereas the mean values of percent lymphocytes remain in the normal range, given the trend for an increase in WBC count, the net effect is an increase in lymphocyte count with Enclomid. This eosinophil result is analogous. There is a clear implication for treating men who have low lymphocytes, such as men who are HIV-positive. Since Enclomid is unlikely to lower lymphocytes based on this result, a case could be made for its use in the population of men with AIDS. These individuals are often treated with agents that are intended to raise testosterone due to the wasting effects of disease. Low liver and kidney toxicity and favorable effects on cholesterol and lipids are also highly favored attributes for any medication intended for use HIV-positive men who are already compromised by their disease.

The increase in serum glucose with Clomid or Zuclomid was within the normal range. In the case of Enclomid where the mean serum glucose values were high on day 0, there were no increases with treatment. There was no evidence that Enclomid would have a deleterious effect on blood glucose.

No clearly adverse effects on liver function are apparent as judged by the enzymes AST and ALT. The trend in these values was a decrease with treatment. An increase in the level of enzymes in the serum would indicate liver damage. ALT/SGPT was out of range low at the end of the study for the Clomid group although the differences over the treatment period were not statistically significant. The changes with Enclomid and Zuclomid were within the normal range. AST is depressed in pregnancy; thus the action of an estrogen agonist such as Zuclomid in lowering the marginal AST level could be rationalized. Alkaline phosphatase (ALP) is also found in the liver and is elevated various disease states. The lowering of ALP argues further against hepatic damage. There were no changes in serum albumin, also a liver product. A strong suppression of serum albumin over an extended time period could contribute to free serum steroid hormone levels in humans although a more important role is played by sex hormone binding globulin. As a bottom line, none of the compounds could be linked to liver damage on the basis of the parameters assayed.

Osteoblastic activity and diseases of the bone are accompanied by high serum ALP values. ALP was not elevated following Zuclomid treatment and was decreased in value following Enclomid treatment. The trends would predict a more benign result for the use of Enclomid compared to Zuclomid.

Although BUN and BUN/creatinine were altered during the study in the Clomid and Enclomid groups, the lack of a definitive change in creatinine argues against renal dysfunction. A loss of glomerular filtration capacity would result in an increase in BUN. Decreased BUN occurs in humans due to poor nutrition (not likely in a controlled setting), or high fluid intake (presumably accompanied by edema). Also, despite an increase in total serum testosterone between day 0 and Day 12 with Enclomid, there were no differences between serum creatinine values, arguing against an increase in muscle mass over this short time interval.

Serum sodium levels were lower than reference values for all animals throughout the study. Serum carbon dioxide was higher than reference values on day 12 for the Clomid and Zuclomid groups. Serum anion gap was lower for all animals throughout the study, paralleling the sodium results. Enclomid raised this parameter towards normal values. The electrolyte imbalances detected in the test animals throughout all treatment periods remains elusive but might be part of the same fluid derangement phenomenon suggested by the BUN results.

Treatment with Enclomid tended to decrease serum cholesterol and Zuclomid tended to increase the same parameter although neither change reached statistical significance. Those changes were within the normal range although the trend for the two isomers to demonstrate opposite effects over a short period of time merits the further monitoring and might not be unexpected given that the isomers have, alternatively, estrogen agonist or antagonist activity. Enclomid might be expected to be more benign than Zuclomid with respect to serum cholesterol if used chronically.

The foregoing results indicate that Enclomid is more effective than Clomid or Zuclomid at enhancing total serum testosterone. Zuclomid is clearly not effective and that deficiency limits any use of Clomid for hypogonadism, particularly since the Zuclomid component of Clomid would predominate in the circulation over time given its longer half-life.

Enclomid appeared to be relatively benign in all aspects when compared to Zuclomid and, often, even Clomid. This is particularly true when consideration is given to the trend of Enclomid to lower cholesterol, and liver enzymes as opposed to Zuclomid's trend to raise the same parameters. The surprising trend for Enclomid to raise the lymphocyte count may be useful for men with AIDS if it can be shown the CD4+ subpopulation of lymphocytes is not lowered or is enhanced.

EXAMPLE 2

Method for Increasing Testosterone Level in Men Using Trans-Clomiphene and Mixtures of Trans-Clomiphene and Cis-Clomiphene at Ratios Greater than 71/29

Prior to administration of trans-clomiphene, blood samples are taken from subject males and testosterone levels are measured using methodologies described for example in Matsumoto, et al. Clin. Endocrinol. Metab. 56; 720 (1983) (incorporated herein by reference). Sex hormone binding globulin (SHBG), both free and bound to testosterone, may also be measured as described for example in Tenover et al. J. Clin. Endocrinol. Metab. 65:1118 (1987) which describe measurement of SHBG by both a [$^3$H] dihydrotestosterone saturation analysis and by radioimmunoassay. Non-SHBG-bound testosterone levels (bioavailable testosterone) are also measured for example according to Tenover et al. J. Clin. Endocrinol and Metab. 65:1118 (1987). See also Soderguard et al. J. Steroid Biochem 16:801 (1982) incorporated herein by reference.

Patients are given daily dosages of 1.5 mg/kg clomiphene, wherein the ratio of trans-clomiphene to cis-clomiphene is greater than 71/29. Patients are monitored for testosterone levels such that the dosage amount and dosage frequency may be adjusted to achieve therapeutic levels of testosterone in the patient.

What is claimed is:

1. A method for treating a condition associated with testosterone deficiency in a human male, comprising administering to a human male with secondary hypogonadism an effective amount of a composition comprising as active ingredient 100% trans-clomiphene or pharmaceutically acceptable salts thereof and optionally one or more pharmaceutically acceptable diluents, adjuvants, carriers or excipient, wherein the condition associated with testosterone deficiency is oligospermia or azoospermia.

2. The method of claim 1, wherein the trans-clomiphene is in a dosage of 1-200 mg per day.

3. The method of claim 2, wherein the trans-clomiphene is in a dosage of 50 mg per day.

4. The method of claim 1 wherein the trans-clomiphene is administered in a dosage of 1.5 mg/kg per day.

5. The method of claim 1, wherein the composition consists essentially of 12.5 mg of trans-clomiphene or a pharmaceutically acceptable salt thereof.

6. The method of claim 1, wherein the composition is in the form of a filled capsule for oral use.

7. The method of claim 1, wherein the composition is in the form of a tablet for oral use.

* * * * *